United States Patent
Bardy (12) 
(10) Patent No.: US 6,238,423 B1
(45) Date of Patent: *May 29, 2001

(54) APPARATUS AND METHOD FOR TREATING CHRONIC CONSTIPATION

(75) Inventor: Gust H. Bardy, Seattle, WA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/409,230

(22) Filed: Sep. 30, 1999

Related U.S. Application Data (63) Continuation of application No. 08/782,842, filed on Jan. 13, 1997, now Pat. No. 6,026,326.

(51) Int. Cl.$^7$ .................................................... A61N 1/00
(52) U.S. Cl. ............................................................ 607/40
(58) Field of Search ............................... 607/40, 41, 116, 607/133, 130

(56) References Cited

U.S. PATENT DOCUMENTS

| | | |
|---|---|---|
| 4,981,470 | 1/1991 | Bombeck, IV . |
| 5,188,104 | 2/1993 | Wernicke et al. . |
| 5,292,344 | 3/1994 | Douglas . |
| 5,540,730 * | 7/1996 | Terry, Jr. et al. ...................... 607/40 |
| 5,690,691 * | 11/1997 | Chen et al. ............................ 607/40 |
| 6,026,326 * | 2/2000 | Bardy .................................... 607/40 |

FOREIGN PATENT DOCUMENTS

| | | |
|---|---|---|
| 0571 938A2 | 5/1993 | (DE) . |
| 2 237 648 | 7/1973 | (FR) . |
| WO 94/27672 | 5/1994 | (GB) . |

OTHER PUBLICATIONS

Electric Stimulation of the Gastrointestinal Tract—GP Apr. 1994.

Gastrointestinal Pacing—A New Concept in the Treatment of Ileus—Biomedical Sciences Instrumentation vol. 1. 1963 (A.M. Bilgutay, R. Wingrove, W.O. Griffen, R.C. Bonnabeau and C.W. Lillehei).

Gastro–intestinal Pacing: Will It Work?—American Journal of Surgery, Feb. 1966 (J. Sonneland).

Evaluation of the Intrinsic Innervation of the Internal Anal Sphincter using Electrical Stimulation—Gut, 1989, 30, 935–938 (M.A. Kamm, J.E. Lennard–Jones, and R.J. Nicholls).

(List continued on next page.)

Primary Examiner—George R. Evanisko
(74) Attorney, Agent, or Firm—Thomas F. Woods; Michael J. Jaro; Harold Patton (57) ABSTRACT

An anticonstipation apparatus, and method, that may include using an implanted stimulus generator that may supply electrical stimuli to the muscles associated with a target portion of the patient's gut, from the esophagus to the anus, through an electrical lead and several pairs of electrodes. The electrical stimuli may be provided to nerves in the autonomic nervous system that are associated with the muscles, or the stimuli may be provided directly to the muscles themselves. The stimuli may be provided sequentially, in a proximal to caudad direction, in order to initiate, enhance or artificially produce peristalsis in the gut's target portion in a proximal to caudad direction. If the gut's target portion is in the descending colon, such stimulation may be coordinated with similar stimulation of the muscles associated with the rectum and anus. A sensor may be provided to detect when the target portion is experiencing constipation.

70 Claims, 6 Drawing Sheets

OTHER PUBLICATIONS

Enhancing Absorption in the Canine Short Bowel Syndrome by Intestinal Pacing—Surgery, Aug. 1980 (H.E. Gladen and K.A. Kelly).

Pacing the Human Stomach—Surgery, Feb. 1992 (B.W. Miedema, M.G. Sarr and K.A. Kelly).

Ectopic Jejunal Pacemakers and Gastric Emptying after Roux Gastrectomy: Effect of Intestinal Pacing—Surgery, Nov. 1989 (L.Karlstrom and K.A. Kelly).

Differential Responses of the Canine Gastric Corpus and Antrum to Electric Stimulation—American Journal of Physiology, Jan. 1974 (K.A. Kelly).

The Electrical Control of Sphincter Incompetence—The Lancet, Jul. 23, 1963 (K.P.S. Caldwell).

Gastric Motor Physiology and Pathophysiology—Surgical Clinics of North America, vol. 73, Dec. 1993 (J.J. Cullen and K.A. Kelly).

The Role of the Extrinsic Antral Nerves in the Regulation of Gastric Emptying—Surgery, Gynecology & Obstetrics, Sep. 1977, vol. 145 (C.T. Mroz and K.A. Kelly).

A New Treatment for Rectal Prolapse—Geriatrics, Jan. 1968 (K.P.S. Caldwell).

Incontinence—Transactions of The Medical Society of London, Ordinary Meeting, Apr., 1973 (K.P.S. Caldwell).

Control of Gastro–intestinal Motility with Electrical Pacing—Jap. J. Smooth Muscle Res. 21: Suppl., 125, 1985 (H.M. Richter, III, S. Bjorck and K.A. Kelly).

Effect of Electrical Stimulation on Gastric Electrical Activity, Motility and Emptying—Neurogastroenterology and Motility 1995 (J.C. Eagon and K.A. Kelly).

Independence of Canine Gastric and Duodenal Pacesetter Potentials Shown by Electric Pacing—May Clin. Proc, Jan. 1977, vol. 52 (H.E. Gladen and K.A. Kelly).

Duodenal–Gastric Refulx and Slowed Gastric Emptying by Electrical Pacing of the Canine Duodenal Pacesetter Potential—Gastroenterology 72:429–433, Mar. 1977 (K.A. Kelly and C.F. Code).

Pacing the Human Gut—The American Journal of Gastroenterology, vol. 89, No. 3, 1994 (D.A. Johnson and E.L. Cattau).

Pacing the Gut—Gastroenterology, Dec. 1992 (K.A. Kelly).

Human Gastric Myoelectric Activity and Gastric Emptying Following Gastric Surgery and With Pacing—1992 Gastroenterological (M.P. Hocking, S.B. Vogel and C.A. Sninsky).

Pacing the Canine Stomach with Electric Stimulation—American Journal of Physiology, Mar. 1972 (K.A. Kelly and R.C. La Force).

Gastric Emptying of Liquids and Solids: Roles of Proximal and Distal Stomach—Editorial Review, The American Physiological Society 1980 (K.A. Kelly).

Electric Pacing of Intact and Transected Canine Small Intestine and its Computer Model—American Journal of Physiology, vol. 229, Nov. 1975 (O.E. Akwari, K.A. Kelly, J.H. Steinbach and C.F. Code).

Electrical Treatment of Anal Incontinence—The Lancet, Feb. 5, 1966 (B.R. Hopkinson, R. Lightwood).

Electrophysiology of Human Colon Motility in Health and Disease—Clinics in Gastroenterology, vol. 15, No. 4, Oct. 1986 (J.D. Huizinga).

Cerebral Evoked Potentials After Rectal Stimulation—Electroencephalography and Clinical Neurophysiology, 80 (1991) 490–495 (V. Loening–Baucke, N.W. Read and T. Yamada).

Measurement of Gastric and Small Bowel Electrical Activity at Laparoscopy—Journal of Laparoendoscopic Surgery, vol. 4, No. 5, 1994 (B.O. Familoni, T.L. Abell and G. Voeller).

Electrical Stimulation of the Bowel—Arch Surg. vol. 91, Sep. 1965 (J.M. Moran and D.C. Nabseth).

Electrical Pacing for Short Bowel Syndrome—Surgery, Gynecology & Obstetrics—Nov. 1981, vol. 153 (H.E. Gladen and K.A. Kelly).

The Treatment of Incontinence by Electronic Implants—Annals of The Royal College of Surgeons of England, Dec. 1967 (K.P.S. Caldwell).

The Future of Intestinal Pacing—Gastroenterology Clinics of North America, vol. 23, No. 2, Jun. 1994 (J.J. Cullen and K.A. Kelly).

Control of Muscle Tone in the Human Colon—Gut, 1992, 33, 541–546 (C.J. Steadman, S.F. Phillips, M. Camilleri, N.J. Talley, A. Haddad, R. Hanson).

Enhancing the Anti–Dumping Effect of Roux Gastrojejunostomy with Intestinal Pacing—Ann. Surgery, Oct. 1983, vol. 198 (B. Cranley, K.A. Kelly, V.L.W. Go, L.A. McNichols).

The Roux Operation for Postgastrectomy Syndromes—The American Journal of Surgery, vol. 161, Feb. 1991 (B.W. Miedema, K.A. Kelly).

Effect of Duodenal Cooling on Small Intestinal Pacing—Mayo Clin. Proc. Aug. 1982, vol. 57 (K.R. Berg, H.E. Gladen, K.A. Kelly).

Achieving Enteric Continence: Principles and Applications—Mayo Clin Proc. Jul. 1986, vol. 61 (J.H. Pemberton, K.A. Kelly).

Electrical Stimulation of the Human Stomach—Digestive Diseases and Sciences, vol. 30, No. 8, Aug. 1985 (W.E. Waterfall, D. Miller, D.N. Ghista).

Temporary and Permanent Electrical Stimulation of the Human Stomach Using High Frequency Pacing—Motility and Nerve–Gut Interactions, Apr. 1993 (B.O. Familoni, T.L. Abell, G. Voeller, A. Salem, O. Gaber, D. Nemoto).

A Model of Gastric Electrical Activity in Health and Disease—IEEE Transactions on Biomedical Engineering, vol. 42, No. 7, Jul. 1995 (B.O. Familoni, T.L. Abell, K.L. Bowes).

Use of Spectral Analysis in the Detection of Frequency Differences in the Electrogastrograms of Normal and Diabetic Subjects—IEEE Transactions on Biomedical Engineering, vol. 35, No. 11, Nov. 1988 (C.J. Pfister, J.W. Hamilton, N. Nagel, P. Bass, J.G. Webster and W.J. Thompkins).

Gastric Motility after Gastric Operations—Surgery Annual 1974 (K.A. Kelly).

Electrical Stimulation of Gastric Electrical Control Activity—American Journal of Physiology, vol. 225, No. 1, Jul. 1973 (S.K. Sarna and E.E. Daniel).

Electrical Pacing of the Roux Limb Resolves Delayed Gastric Emptying—Journal of Surgical Research 42, 635–641 (1987) (A. Sawchuk, D. Canal, J.L. Grosfeld, < Slaughter, G. Gardner, T. O'Connor and D. Behrman).

Gastrointestinal Pacing—Staff Report Meeting –University of Minnesota Medical Bulletin 1965 (A.M. Bilgutay, R. Wingrove, W.O. Griffen, A. Nakib, R.C. Bonnabeau, C.W. Lillehei).

Acceleration of Gastric Emptying with Electrical Stimulation in a Canine Model of Gastroparesis—1992 the American Physiology Society (B–E Bellahsène, C.D. Lind, B.S. Schirmer, O.L. Updike and R.W. McCallum).

A Trial of a Gastro–intestinal Pacemaker—Journal of the Irish Medical Association Jan. 1966 (P.N. Fitzpatrick, and A.W. Chen).

Gastrointestinal Pacemaker—The Lancet, Dec. 7, 1963 (J.M. Sanchez).

Gastrointestinal Pacing—Modern Medicine, Mar. 15, 1965 (A.M. Bilgutay, R. Wingrove, W.O. Griffen, A. Nakib, R.C. Bonnabeau and C. W. Lillehei).

Response to Gastrointestinal Pacing: Antral, Duodenal and Jejunal Motility in Control and Postoperative Patients—Annals of Surgery, Jul. 1966 (T. Berger, J. Kewenter, N.G. Kock).

Evaluation of a Portable Gastric Stimulator—IEEE/9th Annual Conference of the Engineering in Medicine and Biology Society, 1987 (B–E. Bellahsene, R.W. McCallum, O.T. Updike).

Role of Gastric Pacesetter Potential Defined by Electrical Pacing—Canadian Journal of Physiology and Pharmacology, vol. 50, Oct. 1972 (K.A. Kelly and R.C. La Force).

The Endomotorsonde—A New Device for Studying the Gastrointestinal Tract—The American Journal of Medical Electronics, Jul.–Sep. 1964 (J.P.M. D'Haens).

Electronic Pacemakers of the Heart, Gastrointestinal Tract, Phrenic Nerve, Bladder and Carotid Sinus: Current Status—Surgery, Aug. 1966, vol. 60, No. 2 (C.E. Anagnostopoulos, W.W.L. Glenn).

Control of Postoperative Adynamic Bowel in Dogs by Electric Stimulation—vol. IX Trans. Amer. Soc. Artif. Int. Organs, 1963 (D. R. de Villiers, I. Saltiel, A. Nonoyama and A. Kantrowitz).

Reverse Electrical Pacing Improves Intestinal Absorption and Transit Time—Surgery, vol. 100, No. 2, Aug. 1986 (A. Sawchuk, W. Nogami, S. Goto, J. Yount, J.A. Grosfeld, J. Lohmuller, M.D. Grosfeld, and J.L Grosfeld).

External Stimulation of Gastric Antrum and Gastric Secretion—The American Journal of Gastroenterology, vol. 52, No. 6, Dec. 1969 (P. Lott, T. Geisel, N.C. Jefferson and H. Necheles).

Electrical Activity of the Gastric Antrum in Normal Human Subjects—The American Journal of Digestive Diseases, vol. 16, No. 7, Jul. 1971 (H. Monges and J. Salducci).

Gastric Pacemakers—Gastroenterology, vol. 70, No. 2, Feb. 1976 (S.K. Sarna, K.L. Bowes and E.E. Daniel).

Apparatus for Electrical Stimulation of Weakened Peristaltic Activity of the Stomach (Experimental Investigation)—Biomedical Eng. Mar.–Apr. 1973 (M.A. Sobakin and V.A. Shepelev).

Clinical Evaluation of the Gastrointestinal Pacer—Surgery, Gynecology & Obstetrics, Jan. 1965 (D.C. Quast, A.C. Beall and M.E. DeBakey).

Electrostimulation of the Small and the Large Bowel in Dogs—Biomedical Sciences Instrumentation, May, 1969 (G. Járos and C.R. Jansen).

Clinical Experience in Control of Postoperative Adynamic Ileus by Electric Stimulation—Surgical Forum, Vo.. 14, 1963 (D.R. de Villiers, I. Saltiel, A. Nonoyama and A. Kantrowitz).

Electric Treatment of Intestinal Obstruction and Postoperative Paralysis of the Bowel—Journ. A.M.A., Apr. 1, 1911 (W.H. Dieffenbach).

Studies in Electrical Stimulation of the Adynamic Bowel—The American Journal of Gastroenterology, vol. 44, 1965 (A. Kantrowitz).

Electrical Activity of the Gastrointestinal Tract as an Indication of Mechanical Activity—American Journal of Digestive Diseases, vol. 8, 1963 (E.E. Daniel and K.M. Chapman).

Relative Electrical Impedance as Index of Intestinal Viability—Archives of Surgery, vol. 89, Jul. 1964 (L.C. Carey, K. Kayser, E.H. Ellison and D. Lepley).

Controlled Radiological Evaluation of an Intestinal Pacemaker (Peristart)—Scand. J. Gastroent., 1966, vol. 1 (P. Bach–Nielsen, H. Baden and A.M. Christensen).

An Improved Method for Recording and Analyzing the Electrical Activity of the Human Stomach—IEEE Transactions on Biomedical Engineering, vol. 32, No. 11, Nov. 1985 (B.E. Bellahsene, J.W. Hamilton, J.G. Webster, P. Bass and M. Reichelderfer).

Study of Transcutaneous and Intraluminal Measurement of Gastric Electrical Activity in Humans—Medical & Biological Engineering & Computing, Jul. 1987 (B.O. Familoni, Y.J. Kingma and K.L. Bowes).

Human Gastric Myoelectric Activity and Gastric Emptying Following Gastric Surgery and With Pacing—Gastroenterology, 1992, vol. 103, No. 6 (M.P. Hocking, S.B. Vogel and C.A. Sninsky).

Programmer Medtronic 7432 and Memory Mod 7455—Clinical Plan Gastroparesis, Mar. 2, 1994.

Electrical Pacing of the Stomach in Dogs—IEEE, Sep. 1992 (B.O. Familoni, T.L. Abell).

Gastroparesis and the Current Use of Prokinetic Drugs—The Gastroenterologist, vol. 1 No. 2, Jun. 1993 (B.J. Kendall and R.W. McCallum).

Physiology of the Colon and Rectum—The American Journal of Surgery, vol. 117, Jun. 1969 (R.D. Williams and J.W. Dickey).

Effects of Gastric Pacing on Canine Gastric Motility and Emptying—American Journal of Physiology, vol. 265, No. 4, Oct. 1993 (J.C. Eagon and K.A. Kelly).

Manometric Evaluation of Children with Chronic Constipation Using a Suction Stimulating Electrode—Eur. J. Pediatr. Surg. 2 (1992)287–290 (M. Kubota, A. Nagasaki and K. Sunitomo).

* cited by examiner

APPARATUS AND METHOD FOR TREATING CHRONIC CONSTIPATION

This application is a continuation of application Ser. No. 08/782,842, filed Jan. 13, 1997 now U.S. Pat. No. 6,026,326.

BACKGROUND OF THE INVENTION

The present invention relates generally to apparatus and methods for treating constipation in humans. More particularly, it relates to treating chronic, severe constipation by using an anticonstipation apparatus to electrically stimulate the muscles associated with the afflicted portion of the gut. This may be done by stimulating portions of the autonomic nervous system associated with those muscles, or by directly stimulating those muscles themselves.

SUMMARY OF THE INVENTION

Constipation is a life-disturbing problem that afflicts millions of Americans, from the very young to the elderly. Although relatively rare among the young, it is a very common problem in middle age, and is a nearly ubiquitous problem in the elderly.

Chronic constipation is a major problem for many individuals, and frequently causes extreme discomfort to the afflicted. Such discomfort may be a major obstacle to leading a normal life, and may consume an enormous amount of the afflicted person's energy and time.

Besides causing severe discomfort, chronic constipation may also be harmful to the patient. For example, chronic constipation may result in an intestinal obstruction that may cause the patient great pain; or that may even cause the patient's death, unless surgically corrected. Chronic constipation may also prevent the patient from receiving the benefit of certain needed prescription medications, because the medications may have undesirable side effects on an already constipated gut.

Chronic constipation may result, for example, from bowel denervation, a neuro-reflex dysfunction, or a neuro-smooth muscle disorder. Such conditions may arise from such causes as diabetes, spinal injury, or primary degenerative neurologic diseases.

Conventional therapies for chronic constipation are often distasteful and unpleasant, at best, since they may involve such treatments as the repeated consumption of large quantities of laxatives such as milk of magnesia, the repetitive use of enemas, or both. Repeatedly consuming large quantities of laxatives may be harmful to the patient, since they may result in dehydration or even renal failure. The repetitive use of enemas may be harmful since they may irritate or physically harm the treated portion of the patient's gut.

Chronic constipation is usually thought of in association with problems of the large intestine. However, other parts of the patient's gut may also exhibit chronic constipation-like problems, such as the esophagus, the stomach, and less frequently, the small intestine. Such problems may include depressed motility of the esophagus, stomach and/or small intestine.

For simplicity, chronic constipation, or chronic constipation-like problems, of any portion of the patient's gut from the esophagus to the anus will be referred to hereafter as simply "constipation".

In general, the present invention may comprise an apparatus and a method for treating constipation of any portion of the patient's gut from the esophagus to the anus. All, or part, of the apparatus may be located inside of the patient's body.

In basic form, the anticonstipation apparatus of the present invention may comprise an electrical stimulus generator; at least one pair of electrodes; and at least one lead for electrically connecting the pair of electrodes to the stimulus generator. The stimulus generator may include an electrical pulse generator. Any particular pair of electrodes may be anchored at a respective stimulation site to stimulate the muscles associated with the constipated target portion of the gut. The stimulation site may be located on the part of the autonomic nervous system that is associated with those muscles, or the stimulation site may be located directly on those muscles themselves.

When the pulse generator is activated, it may commence production of the desired electrical stimuli. The electrical stimuli may then be conveyed to the gut's target portion by the lead(s) and pair(s) of electrodes.

Only one pair of electrodes may be provided, in which case all of the desired electrical stimuli may be provided to that pair of electrodes. Alternatively, at least two pairs of sequential electrodes may be provided, in which case the desired electrical stimuli may be provided sequentially to the at least two pairs of electrodes.

The electrical stimuli may help to initiate or enhance the patient's natural peristaltic waves in a proximal to caudad direction along at least the gut's target portion, in order to help alleviate the constipation. Alternatively, where the patient's body is incapable of producing any natural peristaltic waves on its own, the electrical stimuli may artificially produce the needed peristaltic waves. When the desired electrical stimulation has been provided, the pulse generator may then be turned off.

The stimulus generator may comprise, in addition to the pulse generator, a controller that may include a suitably programmed microprocessor. The controller may control the pulse generator in such a way that, when the pulse generator is activated, the pulse generator may produce any particular desired stimulus, combination of stimuli, sequence of stimuli, and/or timing of stimuli.

By way of example, the electrical stimulation provided by the pulse generator may comprise monophasic waveform stimuli, biphasic waveform stimuli, and/or multiphasic waveform stimuli.

The anticonstipation apparatus of the present invention may also comprise a constipation sensing means for detecting when a particular portion of the patient's gut is constipated. When a "constipated" signal is received by the controller from the constipation sensing means, the controller may automatically activate the pulse generator; or the controller may alert the patient, or the patient's health care provider, so that the pulse generator may be manually activated.

The anticonstipation apparatus of the present invention may also electrically stimulate other portions of the patient's gut besides the constipated target portion. For example, if the gut's target portion is located in the descending colon, then the apparatus may also electrically stimulate the rectum and/or the anus, in order to aid the patient in defecating.

The method of the present invention may comprise using an anticonstipation apparatus to treat constipation by electrically stimulating the muscles associated with the constipated target portion of the gut. The method may include using the apparatus to electrically stimulate the part of the autonomic nervous system that is associated with those muscles, or to electrically stimulate those muscles themselves. The method may also include electrically stimulating other portions of the patient's gut besides the constipated target portion.

It should be understood that the foregoing summary of the present invention does not set forth all of its features, advantages, characteristics, structures, methods and/or processes; since these and further features, advantages, characteristics, structures, methods and/or processes of the present invention will be directly or inherently disclosed to those skilled in the art to which it pertains by all of the disclosures herein.

DESCRIPTION OF THE PREFERRED EMBODIMENTS

Referring now to the figures, the anticonstipation apparatus 8 of the present invention may comprise a fluid-tight housing 9; a stimulus generator 10, located within the housing 9; an electrical lead 12, and five pairs of stimulating electrodes 14. The housing 9 may be of any suitable construction, such as the construction used for the housings of conventional implanted heart pacemakers or defibrillators. Each part of the anticonstipation apparatus 8 that may be in contact with the patient's body during use of the apparatus 8 may be made from, or coated with, one or more non-toxic, patient-compatible materials, such as polyurethane or silicone.

The primary purpose of the lead 12 may be to convey electrical stimuli from the stimulus generator 10 to the stimulating electrodes 14. However, the lead 12 may also help to properly position and anchor the electrodes 14 with respect to each other, and with respect to the constipated, target portion 17 of the patient's gut. The electrodes 14 may be used to stimulate the muscles associated with the gut's target portion 17 by stimulating portions of the autonomic nervous system associated with those muscles, or by directly stimulating those muscles themselves.

If the muscles are to be made to contract, then the stimulated portion of the autonomic nervous system may comprise the parasympathetic autonomic nervous system. If the muscles are to be made to relax, then the stimulated portion of the autonomic nervous system may also comprise the parasympathetic autonomic nervous system.

The electrodes 14 may be anchored to the lead's electrode portion 11 in any suitable way, such as by gluing, heat welding, ultrasonic welding, stapling or suturing.

Figure 2:
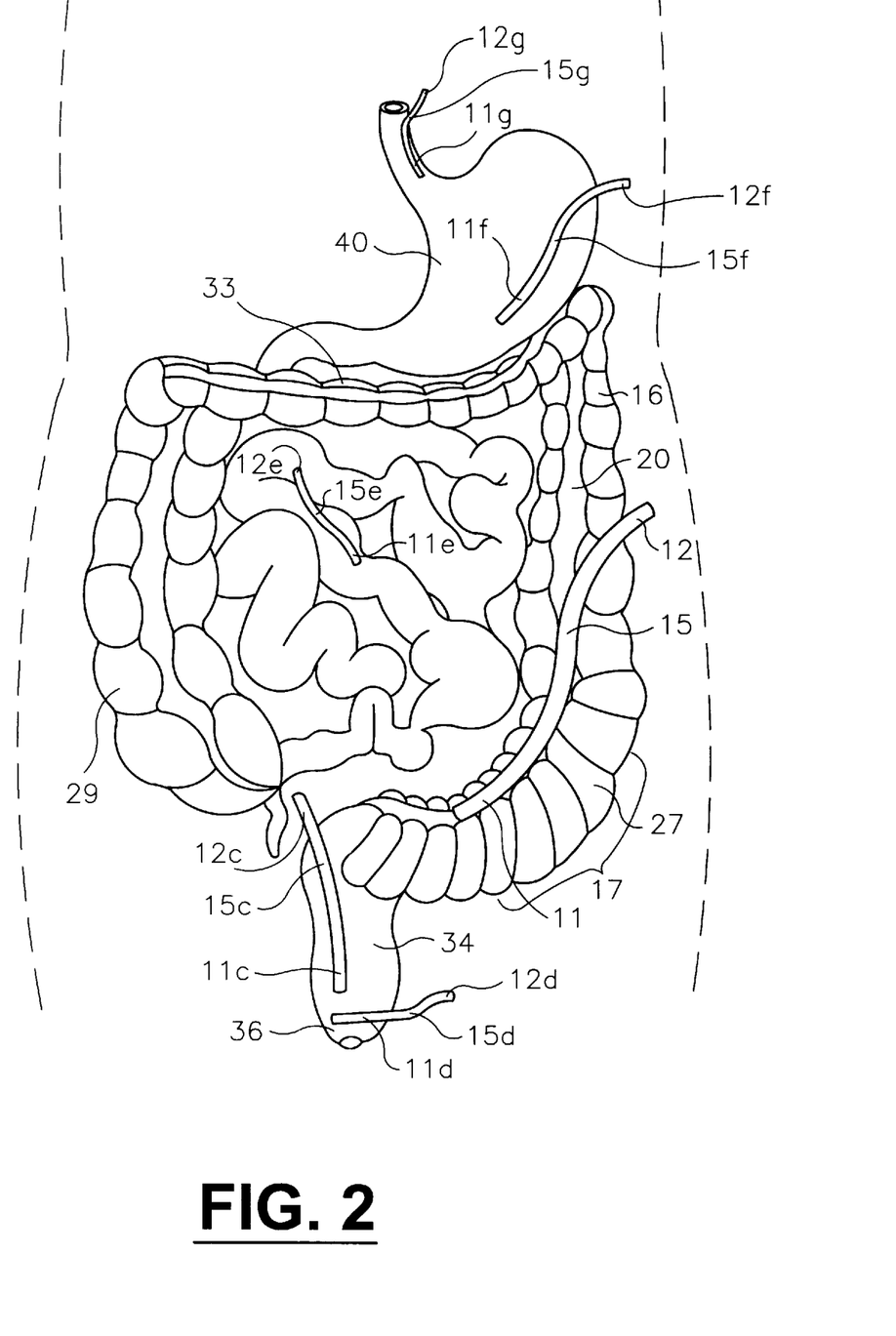
FIG. 2 is an enlarged interior elevational view of the anti-constipation apparatus of the present invention shown installed at various locations on the patient's gut.
Figures 3, 4A, 4B:
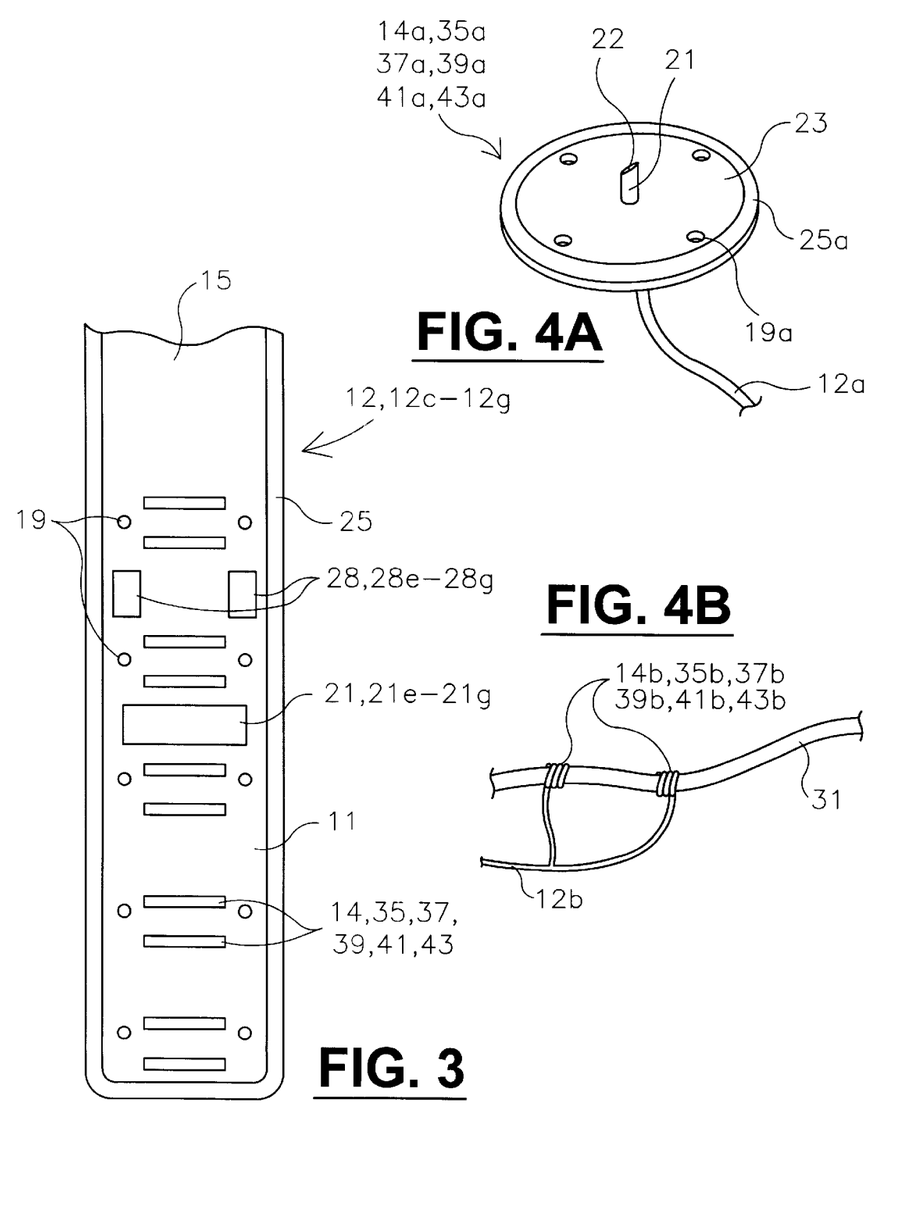
FIG. 3 is an elevational view of one embodiment of the electrode portion of the anticonstipation apparatus' electrical lead.
FIG. 4a is a perspective view of an alternative, needle-type electrode for the anticonstipation apparatus.
FIG. 4b is a perspective view of an alternative, nerve electrode for the anticonstipation apparatus.

As best seen in FIGS. 2 and 3, the lead 12 may have an electrode portion 11 that carries the stimulating electrodes 14; a connecting portion 15 that extends from the electrode portion 11 to the stimulus generator 10; and anchoring holes 19 to assist in stapling or suturing the electrode portion 11 to the gut's target portion 17.

Alternatively, a fibrous cuff 25 may be provided along the periphery of the lead 12, to assist in stapling or suturing the lead's electrode portion 11 to the gut's target portion 17.

The lead 12's electrode portion 11 may have a length from about three to twenty-four inches long, although it may be shorter, or longer, depending on such factors as the length of the gut's target portion 17, and the number and spacing of the stimulating electrodes 14. All other things being equal, the length of the electrode portion 11 may be generally proportionate to the size of the patient, and thus may be shorter for children than for adults.

It may be very important for the lead 12's electrode portion 11 and the stimulating electrodes 14 to be flexible enough: (a) to easily conform to the often convoluted three-dimensional shape of the gut's target portion 17, (b) to not interfere with the contractions and other movements of any portion of the gut, including the gut's target portion 17, and (c) to not harm the gut's target portion 17, or any adjacent organ.

For example, if such flexibility is not provided, the electrode portion 11 and the stimulating electrodes 14 may be difficult to properly install on the gut's target portion 17. In addition, after they are installed, the contractions and other movements of the gut's target portion 17 may cause them to at least partially tear away from the target portion 17. This may prevent the electrode portion 11 and the electrodes 14 from serving their intended purpose, and may even cause injury to the gut's target portion 17, or to adjacent organs. Such injuries may result in very serious consequences for the patient, and may even cause the patient's death.

In order to provide the desired flexibility, the electrode portion 11 may have a generally thin, narrow, ribbon-like configuration. The width of the electrode portion 11 may be from about 5 mm to 10 mm, although it may be narrower, or wider, depending on such factors as the circumference of the gut's target portion 17 and the width of the electrodes 14. All other things being equal, the width of the electrode portion 11 may be generally proportionate to the size of the patient, and thus may be narrower for children than for adults. The thickness of the electrode portion 11 may depend on the flexibility of the materials from which it is made, as well as on its length and width.

It may be important to note that a lead 12 whose electrode portion 11 has a ribbon-like configuration may serve at least three important functions. First, as has been described, the ribbon-like configuration may help to provide the desired flexibility. Second, the ribbon-like configuration may provide a mounting surface that is large enough to enable the electrodes 14 to be easily and securely mounted directly to the electrode portion 11 in any desired spacing and orientation, as best seen in FIG. 3. Third, the ribbon-like configuration may enable the electrodes 14 to be made from very thin, flexible material, since they may be entirely supported by the electrode portion 11, rather than being self-supporting.

Alternatively, instead of there being only one electrode portion 11 of the lead 12 that carries all of the electrodes 14, there may be two, or more, leads 12, each with a respective electrode portion 11; wherein each such respective electrode portion 11 may carry at least one respective electrode 14.

Alternatively, instead of any particular electrode 14 being entirely mounted to the surface of its respective lead 12, all or part of the particular electrode 14 may be free of the surface of its respective lead 12. In such an event, each such particular electrode 14 may be provided with suitable means for anchoring its free portion directly to the gut's target portion 17. Such anchoring means may include anchor holes in its free portion (similar to the lead 12's anchor holes 19), or a fibrous cuff (similar to the lead 12's fibrous cuff 25) that extends along the periphery of its free portion, to help enable the particular electrode 14's free portion to be stapled or sutured to the gut's target portion 17.

Although five pairs of stimulating electrodes 14 on the lead's electrode portion 11 are illustrated in FIG. 3, there may be only one pair of the electrodes 14, or there may be as many as one hundred, or more, pairs of the electrodes 14. The number of pairs of stimulating electrodes 14 may depend on such factors as where in the gut the target portion 17 is located, the size or length of the target portion 17, and the voltages to be applied to each pair of stimulating electrodes 14.

The distance between the electrodes 14 in each pair of the electrodes 14 may be about 2 mm, although that distance may be smaller, or larger, depending on such factors as the number of pairs of the electrodes 14, and the voltages to be applied to each pair of the electrodes 14. For example, the distance between the electrodes 14 in each pair of the electrodes 14 may range from about 1 mm to about 100 mm.

Although the electrodes 14 in each pair of the electrodes 14 are illustrated as being oriented at least generally parallel with respect to each other, they may have any other suitable, effective orientation with respect to each other.

Adjacent pairs of the electrodes 14 may be separated from each other by a distance of from about 1 cm to 10 cm. However, the distance between each pair of the electrodes 14 may be smaller, or larger, depending on such factors as where in the gut the target portion 17 is located, the size or length of the target portion 17, the number of pairs of the electrodes 14 to be used, and the voltages to be applied to each pair of the electrodes 14.

As seen in FIG. 3, the electrodes 14 may be oriented at least generally transversely to the longitudinal centerline of the lead 12's electrode portion 11, so that when the lead 12 is installed at the gut's target portion 17, the electrodes 14 may also be oriented at least generally transversely with respect to the longitudinal centerline of the gut's target portion 17. Alternatively, some, or all, of the electrodes 14 may have any other suitable, effective orientation.

The electrodes 14 may be generally rectangular; may have a width of about 1 mm; and may have a length of about 3 mm. However, the width and/or length of any particular electrode 14 may be smaller, or larger, depending on such factors as where the target portion 17 is located in the gut, and the size and length of the gut's target portion 17. For example, the electrodes 14 may have a width of from about 1 mm to about 10 mm, and a length of from about 2 mm to about 20 mm.

Alternatively, instead of being rectangular, the electrodes 14 may have any other suitable, effective shape.

The electrodes 14 may preferably have a relatively low impedance, in order to increase current sensitivity and to reduce power consumption.

Alternatively, instead of the plate-type electrodes 14 of FIG. 3 that were described in detail above, at least one of the electrodes 14 may comprise an alternative, needle-type electrode 14*a*, as illustrated in FIG. 4*a*. The electrode 14*a* may comprise an electrode needle 21, having a sharp end 22 to help enable the needle 21 to be easily inserted into the tissue to be stimulated. The electrode 14*a* may also comprise a depth-gauge plate 23, to limit how far the needle 21 may penetrate into the gut's target portion 17; several anchoring holes 19*a*; and a fibrous cuff 25*a*. The electrode needle's sharp end 22 may be eliminated if the needle 21 is stiff, and if its diameter is very small. The plate 23 may be electrically conductive and may be in electrical continuity with the needle 21.

Any particular electrode 14*a* may be electrically connected to the stimulus generator 10 by the lead 12, or by a separate lead 12*a*.

If a particular electrode 14*a* is to be anchored to the lead 12's electrode portion 11, it may be so anchored in any suitable way, such as by gluing, heat welding, ultrasonic welding, stapling or suturing its plate 23 to the electrode portion 11. If this is done, then the anchoring holes 19*a* and the fibrous cuff 25*a* may be eliminated.

On the other hand, a particular electrode 14*a* may be a free-standing electrode that is not to be mounted to the lead 12's electrode portion 11. In such a case the electrode 14*a* may be secured to the gut's target portion 17 in any suitable way, such as by using sutures or staples to secure its depth gauge plate 23 to the gut's target portion 17. As seen in FIG. 4, the plate 23 may be provided with anchor holes 19*a* or with a fibrous cuff 25*a* to aid in such suturing or stapling.

The installation of the anticonstipation apparatus 8 in the patient's body will now be addressed. By way of example, it will be assumed that the gut's target portion 17 may be any part, or even all, of the patient's descending colon 16, including the sigmoid colon. However, in addition or as an alternative, the target portion 17 may be any part, or even all, of the ascending colon 29 and/or the transverse colon 33.

Figure 1:
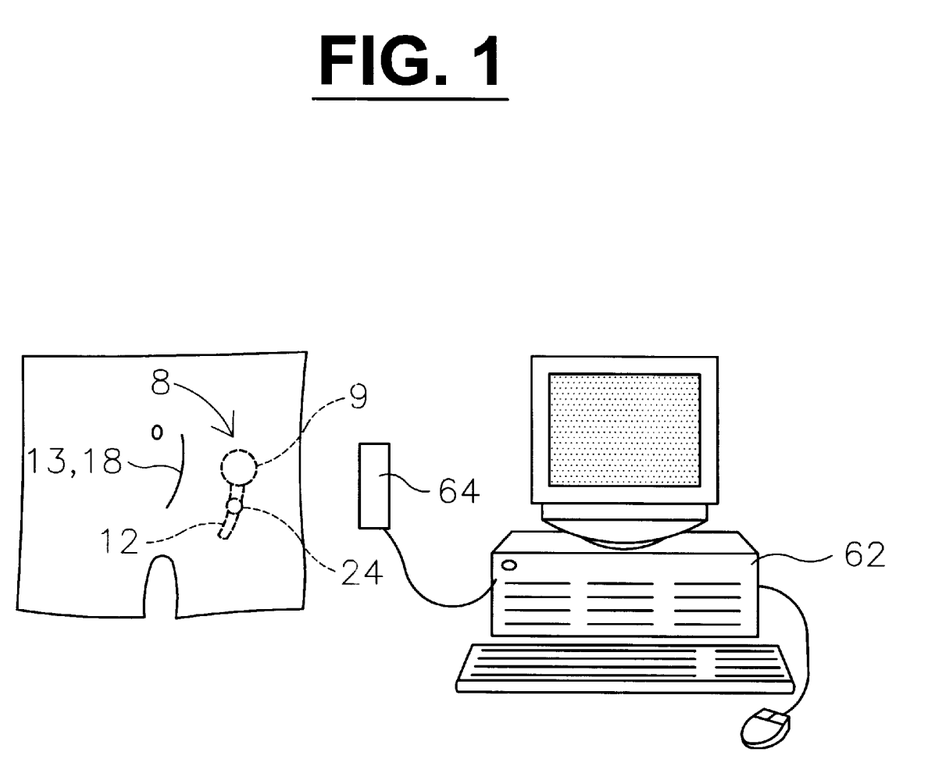
FIG. 1 is an exterior elevational view of the anti-constipation apparatus of the present invention show installed along a patient's descending colon.

Referring now to FIGS. 1 and 2, a periumbilical surgical entrance site 13 may be made in the patient's abdomen for forming an abdominal subcutaneous pocket between the abdominal rectus muscles and the skin. The anticonstipation apparatus 8 may then be inserted into the abdominal subcutaneous pocket through the entrance site 13, and the housing 9 may be anchored to the fascia of the abdominal rectus muscles, such as with sutures or staples. The housing 9, with its stimulus generator 10, may be left in the abdominal subcutaneous pocket until the anticonstipation apparatus 8 is no longer needed by the patient; or until the battery in its power supply 48 needs to be replaced.

A laparoscope may then be used to insert the electrode portion 11 of the lead 12 through a laparoscopy entrance site 18 in the abdominal rectus muscles, and into the patient's abdominal cavity along the target portion 17 of the descending colon 16.

The electrode portion 11 may be positioned so that its electrodes 14 are located on top of, or near to, the target portion 17's principal nervous plexus. That nervous plexus may be located in the target portion 17's adventitia 20, and may be part of the patient's parasympathetic autonomic nervous system.

Prior to anchoring the electrode portion 11 to the adventitia 20 of the target portion 17, the surgeon may "map" the target portion 17's principal nervous plexus, in order to better determine how to achieve the desired results. The desired results may be to cause contractions of the muscles associated with the gut's target portion 17, in order to help initiate, enhance, or artificially produce the peristaltic waves needed to move the contents of the gut's target portion 17 in a proximal to caudad direction.

Such mapping may be done by placing the electrode portion 11, with its electrodes 14, at various locations along the target portion 17's principal nervous plexus. Then for each location, the surgeon may selectively activate various pairs of the electrodes 14 with various electrical stimuli. This may be done by pre-programming the stimulus generator 10; by using the external work station 62, with its telemetry means 64; or by utilizing some combination of both of those techniques.

During the mapping process the surgeon may observe the reaction of the gut's target portion 17 to the applied electrical stimuli, in order to better determine such matters as: (a) exactly where the electrode portion 11, with its electrodes 14, should be located with respect to the target portion 17's principal nervous plexus; (b) which of the electrode pairs 14 should actually be used for stimulation; and/or (c) which electrical stimuli should be used, in order to best achieve the desired results.

After the mapping process has been completed, the surgeon may then anchor the lead 12's electrode portion 11 to the target portion 17's descending colonic adventitia 20 in the desired location; so that the electrodes 14 are, in turn, properly located on top of, or near to, target portion 17's principal nervous plexus.

Such anchoring may be done by using any suitable means, such as by using sutures or staples that are passed through the anchoring holes 19 or the fibrous cuff 25 of the electrode portion 11.

The anticonstipation apparatus 8 may also comprise a constipation sensing means for detecting when the target portion 17 of the descending colon 16 is experiencing constipation. Such constipation sensing means may be useful in situations where the patient may be unconscious, or otherwise unaware of the state of his or her gut. Such constipation may be evidenced by the target portion 17 exhibiting movements that are reduced, or even absent; and/or by exhibiting fullness, or excessive fullness.

The constipation sensing means may comprise any suitable mechanical/electrical transducer 24, such as a saddle 45, a motion sensor 24, a pressure sensor 24 or a strain gauge 24. The transducer 24 may be connected to the stimulus generator 10 by an electrical lead 26 that may be located at least partially within the lead 12.

Figure 8:
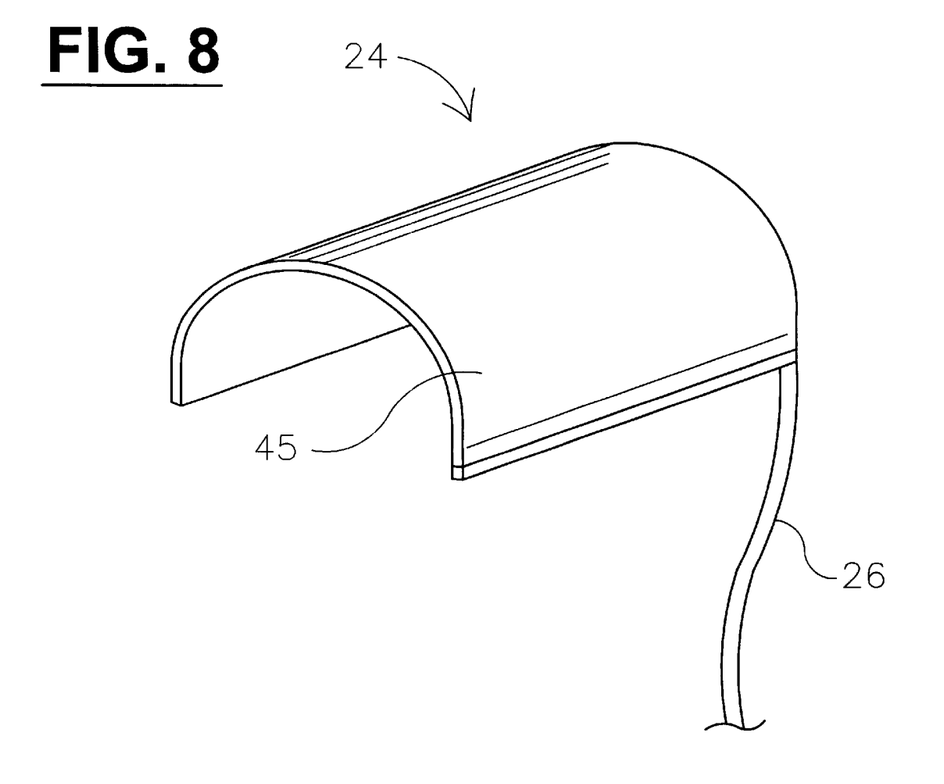
FIG. 8 is a perspective view of a constipation sensor.

For example, as seen in FIG. 8, the transducer 24 may comprise a flexible saddle 45 that may be sized to fit over the outer surface of the target portion 17 of the descending colon 16. The saddle 45 may be secured to the target portion 17 in any suitable way, such as by suturing or stapling. The saddle 45 may be provided with sensing means, such as one or more electrical strain gauges or compression gauges, for detecting the shape of the saddle 45. The saddle 45 may be connected to the stimulus generator 10 by an electrical lead 26 that may be located at least partially within the lead 12.

A normal, unconstipated, descending colon target portion 17 may have a given, pre-determined diameter, or shape; thereby imparting a given shape, or curvature, to the saddle 45. Thus, the stimulus generator 10's microprocessor controller 54 may be programmed to recognize that it has received a "constipated" signal from the saddle 45 when it receives from the saddle 45 signals indicating that the saddle 45's shape, or curvature, corresponds to that of a constipated descending colon 16.

Alternatively, the transducer 24 may comprise a motion sensor 24 for detecting the movements, the strength of the movements or the lack of any movements, of the descending colon's target portion 17. The motion sensor 24 may comprise any suitable motion sensor, such as any conventional piezoelectric motion sensor. A normal, unconstipated, descending colon target portion 17 may produce on the average a predetermined number of peristaltic waves, each having a predetermined minimum strength, during any given time period. Thus, the stimulus generator 10's microprocessor controller 54 may be programmed to recognize that it has received a "constipated" signal from the motion sensor 24 when it receives from the motion sensor 24 signals equal to less than the predetermined number of peristaltic waves, each having the predetermined minimum strength, during any given time period. The controller 54, and how it may be programmed, will be addressed below in more detail.

Alternatively, the transducer 24 may comprise a sensor, such as a pressure sensor 24 or a strain gauge 24, for detecting the fullness, or the overfullness, of the descending colon's target portion 17. If the transducer 24 comprises a pressure sensor 24, then the stimulus generator 10's controller 54 may be programmed to recognize that it has received a "constipated" signal from the pressure sensor 24 when it receives from the pressure sensor 24 a signal that corresponds to a pressure greater than that exhibited by a normal, unconstipated descending colon target portion 17. In a like fashion, if the transducer 24 comprises a strain gauge 24, then the controller 54 may be programmed to recognize that it has received a "constipated" signal from the strain gauge 24 when it receives from the strain gauge 24 a signal that corresponds to a strain greater than that exhibited by a normal, unconstipated descending colon target portion 17.

The mechanical/electrical transducer 24 may be secured in its desired location on the descending colon's target portion 17 in any suitable way, such as by being secured to the lead 12's electrode portion 11, as seen in FIG. 3. Alternatively, the transducer 24 may be secured directly to the target portion 17 itself, such as by the use of sutures or staples.

Alternatively, the constipation sensing means may comprise an electrical sensor comprising at least one pair of spaced apart sensing electrodes 28. The sensing electrodes 28 may be any suitable electrodes, such as plate-type electrodes or needle-type electrodes, and may be similar to the electrodes 14, 14a that were described above.

The sensing electrodes 28 may be secured in their desired locations on the descending colon's target portion 17 in any suitable way, such as by being secured to the lead 12's electrode portion 11, as seen in FIG. 3. Alternatively, the sensing electrodes 28 may be secured directly to the target portion 17 itself, such as by the use of sutures or staples. The electrodes 28 may be oriented with respect to each other along a circumference of the target portion 17; and may be spaced away from each other by any suitable distance, such as by about_of the circumference of the target portion 17.

The sensing electrodes 28 may measure the impedance of the wall of the guts' target portion 17. As the target portion 17 fills, its wall stretches, thereby increasing the impedance measured by the electrodes 28. The controller 54 may be programmed to recognize that it has received a "constipated" signal from the sensing electrodes 28 when the impedance between the sensing electrodes 28 is greater than the impedance that would be exhibited by a normal, unconstipated descending colon target portion 17. The sensing electrodes 28 may be electrically connected to the stimulus generator 10 by electrical leads 30 that may be located at least partially within the lead 12.

Alternatively, the constipation sensing means may be eliminated, such as if not desired, or if the patient is able to directly feel, in a normal manner, when the gut's target portion 17 is constipated. If the constipation sensing means are eliminated, the stimulus generator 10 may be activated manually, or it may be activated automatically according to a schedule that has been pre-programmed into the stimulus generator's controller 54.

Figure 5:
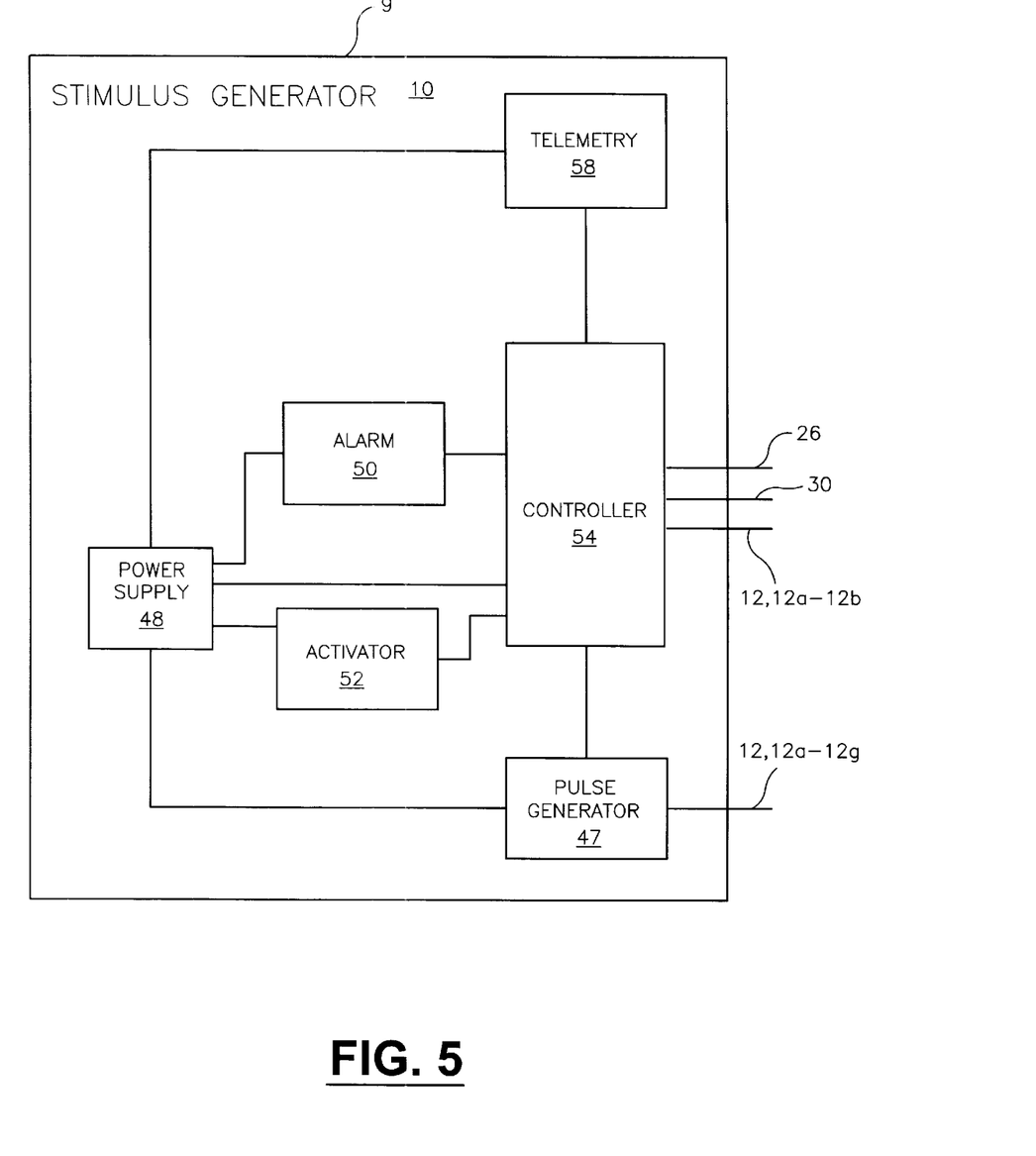
FIG. 5 is a simplified, functional block diagram for the stimulus generator of the anticonstipation apparatus.

Referring now to FIG. 5, the stimulus generator 10, which may be located within the housing 9, may comprise a pulse generator 47; a power supply 48, that may include one or more batteries and any needed voltage regulating means; an alarm 50; an activator 52; a microprocessor controller 54; and a telemetry means 58.

Alternatively, instead of being located within the housing 9, one or more, or all, of the components 47, 48, 50, 52, 54 and 58 may be located on the lead's electrode portion 11 and/or on its connecting portion 15. Each such component may be provided with suitable electrical connections with the other parts of the anticonstipation apparatus 8, such as by means of a suitably modified lead 12, electrode portion 11, and/or connecting portion 15. Each such component may also be protected, such as with a protective coating or by being located within one or more housings that may be located on the lead's electrode portion 11 and/or connecting portion 15.

In addition, or alternatively, the connecting portion 15 of the lead 12 may be eliminated. In such an event, the lead's electrode portion 11 may include telemetry means for receiving information and/or power that is transmitted by the stimulus generator 10's telemetry means 58. The electrode portion 11's telemetry means may be provided with suitable electrical connections with the other parts of the anticonstipation apparatus 8 that may be located on the electrode portion 11, such as by means of a suitably modified electrode portion 11 of the lead 12. The telemetry means for the lead's electrode portion 11 may also be for sending information from the lead's electrode portion 11 (and from any of the stimulus generator 10's components that may be located on the electrode portion 11), to the stimulus generator 10's telemetry means 58.

The voltage regulating means of the power supply 48 may be for providing any needed voltage regulation, multiplication or division, in order to supply any needed voltage(s) for the other components of the stimulus generator 10. Alternatively, the voltage regulating means in the power supply 48 may be eliminated, and the rest of the components of the stimulus generator 10 may be designed to operate directly from the battery(ies) in the power supply 48.

The battery(ies) in the power supply 48 may comprise any highly reliable, long life battery, like those used to energize implantable medical devices such as cardiac pacemakers or defibrillators. Such batteries may include lithium vanadium oxide batteries.

The stimulus generator 10 may be adapted to be used with a suitably programmed external computer work station 62. The work station 62 may include telemetry means 64.

The telemetry means 58 of the anticonstipation apparatus 8 may be for sending information from the apparatus 8 to an external receiver, such as to the telemetry means 64 of the external computer work station 62. Such information may include data regarding the status of the various components of the apparatus 8; the programming of the controller 54; the signals received from the constipation sensors 24, 28; the time and frequency of use of the apparatus 8; the status of the battery in the power supply 48; whether the apparatus 8 was used manually or automatically; and any information stored in the controller 54. The telemetry means 58 may also be for receiving information from an external transmitter, such as from the telemetry means 64 of the work station 62.

The telemetry means 64 of the work station 62 may be for sending information from the work station 62 to the telemetry means 58 of the anticonstipation apparatus 8. Such information may include commands and programming. The telemetry means 64 may also be for receiving information from the telemetry means 58 of the anticonstipation apparatus 8.

The controller 54 may be programmed or re-programmed in any suitable way, such as by using the external work station 62 and the telemetry means 64, 58. If the stimulus generator 10 is to be located within the patient's body, such programming or re-programming may be done either before or after the generator 10 is implanted in the patient's body.

The controller 54 may be programmed in such a way that when it receives a "constipated" signal from the sensing means 24, 28 via their leads 26, 30, it may then automatically activate the alarm 50 to alert the patient, or the patient's heath care provider, that the gut's target portion 17 is full. The alert provided by the alarm 50 may be, for example, an audible alert; a vibratory alert; or a visual alert (if the stimulus generator 10 is located outside of the patient's body).

In addition, or as an alternative, the controller 54 may be programmed so that when it receives a "constipated" signal from the sensing means 24, 28, it may send a suitable alarm signal to the external computer work station 62 via the telemetry means 58, 64. The work station 62 may include a visual or audible alarm that may be activated upon receipt of an alarm signal from the controller 54 to alert the patient, or the patient's health care provider, that the gut's target portion 17 is full.

The controller 54 may be programmed to store pertinent information, such as its programming; the signals it receives from the constipation sensing means 24, 28; the data it receives from any other component of the stimulus generator 10; the activation history of the pulse generator 471; and the electrical stimuli produced by the pulse generator 47 each time it was activated. The controller 54 may also be programmed to send that pertinent information to the external computer work station 62, via the telemetry means 58, 64 on a continuous basis, automatically at predetermined times or intervals, or upon demand from the work station 62.

When the patent or the patient's health care provider is alerted by the alarm 50 or by the external computer work station 62 that the gut's target portion 17 is full, the patient may then be provided with a toilet or a bedpan. Alternatively, the patient may be provided with a toilet or a bedpan upon demand; when a predetermined interval of time has passed since the patient's last bowel movement; or when the patient feels, in an normal fashion, that the target portion 17 of his or her gut is full.

At that time, the activator 52 in the stimulus generator 10 may be activated by the patient or by the patient's health care provider, and send a suitable activation signal to the microprocessor controller 54. The activator 52 may comprise a magnetic switch that may be activated by passing an external, hand-held magnet over the activator 52. Alternatively, the activator may comprise any other suitable mechanical and/or electrical switch.

Alternatively, the patient or the patient's health care provider may use the external computer work station 62 and the telemetry means 64, 58 to send an activation signal to the microprocessor controller 54. Alternatively, the controller 54 may be programmed so that the pulse generator 47 may be controlled directly from the work station 62.

The controller 54 may be programmed so that, upon receipt of the activation signal from the activator 52, or from the work station 62, the controller 54 may then automatically control the pulse generator 47. Alternatively, in certain circumstances, such as when the patient is unconscious and is diapered, the controller 54 may be programmed to automatically control the pulse generator 47 at predetermined intervals without needing any activation from the patient or the patient's health care provider.

The controller 54 may automatically control the pulse generator 47 in such a way that the pulse generator 47 may produce and deliver to gut's target portion 17, via the lead 12 and its stimulating electrodes 14, the particular desired electrical stimuli. The electrical stimuli from the controller 54 and the pulse generator 47 may be selected to cause the muscles in the gut's target portion 17 to contract in such a way so as to urge the contents of the gut's target portion 17 to move in a proximal to caudad direction, thereby helping to alleviate constipation of the target portion 17.

For example, if there is only one pair of the electrodes 14, the controller 54 and the pulse generator 47 may provide all of the electrical stimuli to that single pair of electrodes 14.

Alternatively, if there are two, or more pairs of electrodes 14, the controller 54 and the pulse generator 47 may provide at least one set of sequential electrical stimuli to the successive pairs of stimulating electrodes 14, in a proximal to caudad direction. Such a sequence of electrical stimuli may help to initiate or reinforce the patient's normal peristaltic waves, or to help produce artificial peristaltic waves, along the gut's target portion 17 in a proximal to caudad direction. The timing and strength of the sequential stimuli may be selected to produce, or at least partially produce, what would otherwise be normal, healthy peristaltic waves for the gut's target portion 17.

More than one set of the sequential electrical stimuli may be used, in order to produce multiple peristaltic waves along the gut's target portion 17. In general, each set of the sequential electrical stimuli may produce one peristaltic wave along the gut's target portion 17.

The controller 54 may also be programmed to automatically turn the pulse generator 47 off once all of the desired electrical stimuli have been delivered by the pulse generator 47 to the electrodes 14. In order to avoid accidental, and possibly harmful, over-use of the anticonstipation apparatus 8, the controller 54 may also be programmed to limit how often or how long it may permit the pulse generator 47 to produce electrical stimuli.

Figure 6:
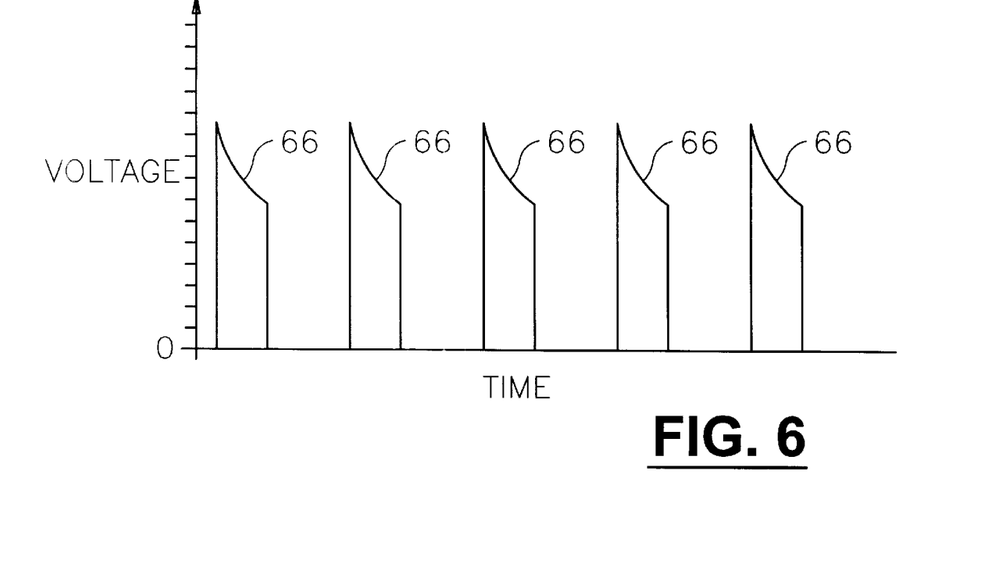
FIGS. 6–7 are graphical depictions of various electrical stimuli that may be used by the anticonstipation apparatus.

Referring now to FIG. 6, it illustrates one set of five sequential electrical stimuli 66 that may be provided by the controller 54 and the pulse generator 47 for the five pairs of electrodes 14. That is, each pair of the electrodes 14 may be provided with one stimulus 66 in any particular set of sequential electrical stimuli 66. Since there may be up to one hundred, or more, pairs of the electrodes 14, the pulse generator 47 may have to produce up to one hundred, or more, stimuli 66 in any particular set of sequential stimuli 66.

Each electrical stimulus waveform 66 may be termed to be "monophasic", since it is of only one polarity, either positive or negative. Each stimulus 66 may comprise a truncated, exponentially decaying waveform having a maximum voltage of about 10.5 volts, a minimum voltage of about 6.8 volts, and a slope of about 65% between the maximum and minimum voltages. Each stimuli 66 may have a pulse width of about 210 microseconds, and adjacent stimuli 66 may be separated from each other by a time interval of about 500 microseconds.

Although the five stimuli 66 in the set of sequential stimuli 66 illustrated in FIG. 6 are shown as being identical, and as being separated by identical time intervals, the stimuli 66 in any particular set of sequential stimuli may not be identical, and may be separated from each other by differing time intervals. Similarly, although a respective stimulus 66 is illustrated in FIG. 6 as being provided for each of the five pairs of electrodes 14, not all of the pairs of electrodes 14 may be provided with a stimulus 66 in any given set of sequential stimuli 66. In addition, in any given set of sequential stimuli 66 at least one of the pairs of electrodes 14 may receive from one to about one hundred stimuli 66.

Although each stimulus 66 is illustrated as comprising a single truncated, exponentially decaying waveform, any other suitable waveform may be used, such as a square wave. In addition each stimulus 66 may comprise a set of higher frequency stimuli, much in the way that analog signals may be digitized, i.e., synthesized by a set of higher frequency discrete digital signals.

Any particular stimulus 66 may have maximum and minimum voltages that range from about 20 microvolts to about 50 volts; and a pulse width that may range from about 20 microseconds to about 20 milliseconds. The time interval between any two adjacent stimuli 66 may range from about 20 microseconds to about 1 millisecond.

During any given operation of the pulse generator 47, the number of sets of sequential stimuli 66 that are generated by it may range from one set to about 10 sets. The sets of sequential stimuli 66 may, or may not, be identical in some or all of their characteristics. If there are at least two sets of sequential stimuli 66, the time interval between any two adjacent sets may range from about 20 microseconds to about 60 seconds. If there are at least three sets of sequential stimuli 66, the time interval between any two adjacent set may not be identical.

Figure 7:
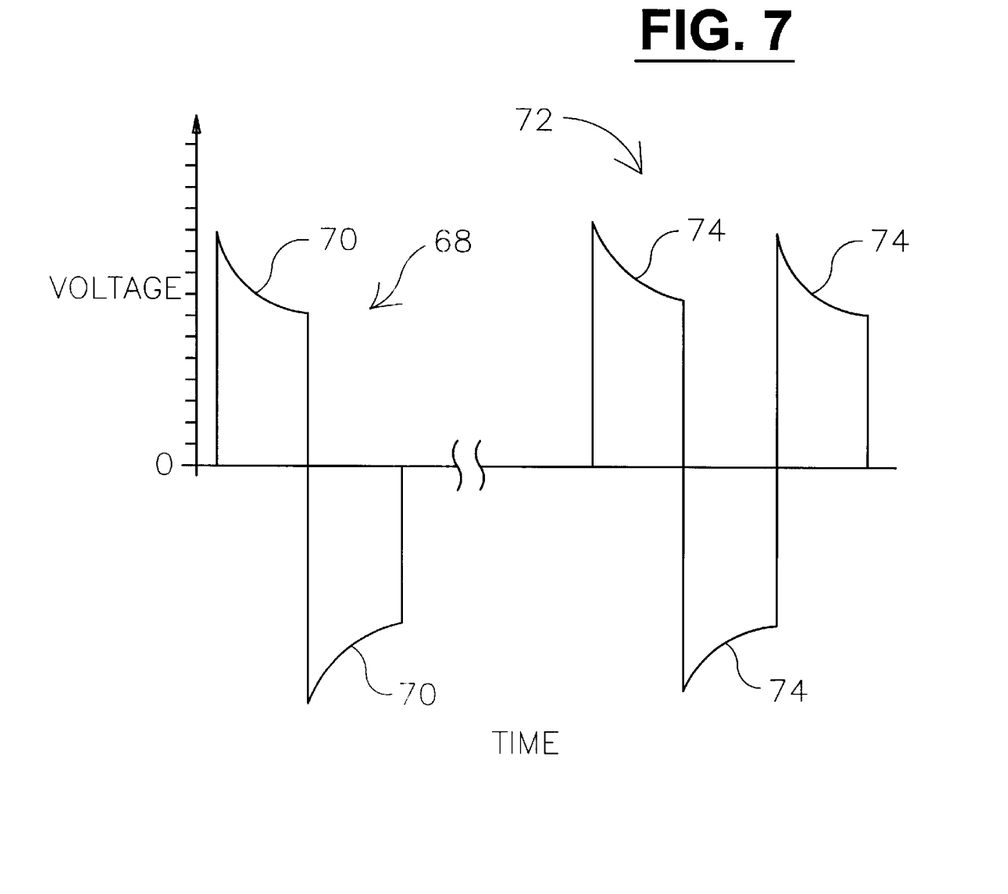

Referring now to FIG. 7, one or more of the stimuli 66 illustrated in FIG. 6 may be replaced by the alternative stimulus 68 seen in FIG. 7. The stimulus 68 may be termed to be "biphasic", since it comprises two stimuli 70, of opposite polarity. Each stimulus 70 may have characteristics that are the same as, or similar to, those described above regarding the stimuli 66. Although the two stimuli 70 are illustrated as being identical, they may not be identical in one, or more, of their characteristics. The biphasic stimulus 68 may have, in its entirety, any other overall waveform, such as sinusoidal. For example, the biphasic stimulus 68 may comprise one full sinusoidal waveform.

Alternatively, one or more of the stimuli 66 illustrated in FIG. 6 may be replaced by the alternative stimulus 72 seen in FIG. 7. The stimulus 72 may be termed to be "multiphasic", since it comprises at least three stimuli 74, of alternating polarity. Each stimulus 74 may have characteristics that are the same as, or similar to, those described above regarding the stimuli 66. Although the three stimuli 74 are illustrated as being identical, they may not be identical in one, or more, of their characteristics. Although the stimulus 72 is illustrated as comprising three stimuli 74, it may comprise up to about 10 stimuli 74. The multiphasic stimulus 72 may have, in its entirety, any other overall waveform, such as sinusoidal. For example, any two adjacent stimuli 74 may comprise one full sinusoidal waveform. Similarly, any three adjacent stimuli 74 may comprise 1½ full sinusoidal wave forms, and so on.

Alternatively, as has been mentioned, if there is only one pair of the electrodes 14, the controller 54 and the pulse generator 47 may provide all of the electrical stimuli to that single pair of electrodes 14. In such an event, the one pair of electrodes 14 may be provided with from one to ten sets of uniphasic stimuli 66, biphasic stimuli 68 and/or multiphasic stimuli 72. Each such set may comprise from one to about one hundred stimuli 66, 70, and/or 74. The separation between adjacent stimuli 66, 70 and/or 74 in each set may range from about twenty microseconds to about one millisecond. If there are at least three stimuli 66, 70 and/or 74, the time interval between any two adjacent such stimuli may not be identical. If there are at least two such sets of stimuli, the time interval between any two adjacent sets may be from about 20 microseconds to about 60 seconds. If there are at least three sets, the time interval between any two adjacent sets may not be identical.

In the foregoing description of the invention, the muscles associated with the descending colon's target portion 17, such as the muscles in the wall of the target portion 17, were stimulated to contract by providing electrical stimuli 66, 68, 72 to the principal nervous plexus in the adventitia 20 of the target portion 17.

As an alternative, and referring now to FIG. 4b, at least one remote part 31 of the autonomic nervous system, that is not located in the adventitia 20 of the target portion 17, may be stimulated instead of, or in addition to, stimulating the principal nervous plexus in the adventitia 20 of the target portion 17. Each remote part 31 may be selected such that when it is electrically stimulated corresponding muscles associated with the descending colon's target portion 17, such as the muscles in the wall of the target portion 17, may contract. The remote part 31 may be part of the patient's vagus nerve.

Electrical stimulation of any particular remote part 31 may be provided by one or more of the electrodes 14, 14a, which may be secured in a suitable location near the particular remote part 31. Alternatively, at least one pair of the FIG. 4b nerve electrodes 14b may be used to provide electrical stimulation to the particular remote part 31. As seen in FIG. 4b, each nerve electrode 14b may be wrapped about a corresponding portion of the remote part 31. The nerve electrodes 14b may be electrically connected to the stimulus generator 10 by an electrical lead 12b. A portion of the lead 12b may be anchored, as with a suture or a staple, to a convenient nearby part of the patient's body. The nerve electrodes 14b may be similar to those described in U.S. Pat. No. 5,263,480.

As an alternative to, or in addition to, stimulating the nerves in the descending colonic adventitia 20 or in a remote part 31 of the autonomic nervous system, at least one muscle associated with the descending colon's target portion 17, such as at least one muscle in the wall 27 of the descending colon's target portion 17, may be stimulated directly by at least one corresponding electrode 14, 14a, in order to cause it to contract.

This may be done by anchoring part or all of the lead's electrode portion 11 and/or the electrodes 14, 14a directly to the wall 27 of the colon's target portion 17. One or more of the electrodes 14, 14a may be located on the exterior surface of the wall 27. Alternatively, one or more of the electrodes 14, 14a may be located in the tissues of the wall 27 itself; or may be located on the interior surface of the wall 27, within the target portion 17's lumen.

In addition to stimulating the muscles associated with the descending colon's target portion 17 in one or more of the ways described above, it may also be desirable to coordinate such stimulation of the colon's target portion 17 with electrical stimulation of the muscles associated with other target portions of the patient's gut, such as target portions of patient's rectum 34 or anus 36.

The target portion of the rectum 34 may comprise all, or part, of the rectum 34. Electrically stimulating the muscles associated with the rectum 34's target portion may be done in a manner which may be the same as, or similar to, that described above regarding stimulating all, or part, of the muscles associated with the descending colon's target portion 17. Thus, stimulation of the muscles associated with the rectum 34's target portion may be provided by rectal electrodes 35, 35a and 35b that may be the same as, or similar to, the electrodes 14, 14a and 14b, respectively. The electrodes 35, 35a, 35b may be connected to the stimulus generator 10 through a lead 12c that may be the same as, or similar to the leads 12, 12a and 12b. If the lead 12c has an electrode portion 11c and a connecting portion 15c, they may be the same as, or similar to, the electrode portion 11 and the connecting portion 15, respectively, of the lead 12.

A goal of such stimulation of the muscles associated with the rectum 34's target portion may be to help move the contents of the rectum 34 in a proximal to caudad direction, such as by causing some or all of the muscles associated with the rectum 34's target portion to contract simultaneously, or by causing some or all of the muscles associated with the rectum 34's target portion to sequentially contract in a proximal to caudad direction.

As was mentioned above, such stimulation of the muscles associated with the rectum 34's target portion may be coordinated with the stimulation of the muscles associated with the descending colon's target portion 17. In particular, when the muscles associated with the colon's target portion 17 have been stimulated, to move its contents towards or into the rectum 34, the muscles associated with the rectum 34's target portion may be stimulated at the same time, or may be stimulated shortly thereafter, to help evacuate the rectum 34.

The target portion of the anus 36 may comprise all, or part, of the anus 36. Electrically stimulating the muscles associated with the anus 36's target portion may be done in a manner which may be the same as, or similar to, that described above regarding stimulating the muscles associated with the descending colon's target portion 17. However, the goal of such anal stimulation may be to relax, rather than to contract, all, or part, of the muscles associated with the anus 36's target portion, in order to help permit evacuation through the anus 36.

Such stimulation of the muscles associated with the anus 36's target portion may be provided by anal electrodes 37, 37a and 37b that may be the same as, or similar to, the electrodes 14, 14a and 14b, respectively. The electrodes 37, 37a, 37b may be connected to the stimulus generator 10 through a lead 12d that may be the same as, or similar to, the leads 12, 12a and 12b. If the lead 12d has an electrode portion 11d and a connecting portion 15d, they may be the same as, or similar to, the electrode portion 11 and the connecting portion 15, respectively, of the lead 12.

The stimulation of the muscles associated with the anus 36's target portion may be coordinated with the stimulation of the muscles associated with the gut's target portion 17 and/or with the stimulation of the muscles associated with the rectum 34's target portion. Such anal stimulation may occur before, during or after such stimulation of the muscles associated with the colon's target portion 17 and/or the rectum 34's target portion, to help cause the muscles associated with the anus 36's target portion to relax, to thereby help permit the patient to defecate.

One preferred manner of coordinating such stimulation may be to sequentially provide such stimulation to the muscles associated with the colon's target portion 17, the rectum 34's target portion, and the anus 36's target portion, so that the contents of the gut may be sequentially moved from the colon's target portion 17, to the rectum 34, and out of the anus 36.

The anticonstipation apparatus of the present invention may also be used to treat constipation of all, or part, of the small intestine 38. Thus, the target portion of the small intestine 38 may comprise all, or part, of the small intestine 38. Electrically stimulating the muscles associated with the small intestine 38's target portion may be done in a manner which may be the same as, or similar to, that described above regarding stimulating the muscles associated with the descending colon's target portion 17. Thus, such stimulation of the muscles associated with the small intestine 38's target portion may be provided by small intestine electrodes 39, 39a and 39b that may be the same as, or similar to, the electrodes 14, 14a and 14b, respectively. The electrodes 39, 39a, 39b may be connected to the stimulus generator 10 through a lead 12e that may be the same as, or similar to the leads 12, 12a and 12b. If the lead 12e has an electrode portion 11e and a connecting portion 15e, they may be the same as, or similar to, the electrode portion 11 and the connecting portion 15, respectively, of the lead 12. The electrode portion 11e may include constipation sensing means 21e, 28e, that may be the same as, or similar to, the constipation sensing means 21, 28 of the lead 12. The electrical leads for the constipation sensing means 21e, 28e may be the same as, or similar to, the electrical leads for the sensing means 21, 28, respectively.

A goal of such stimulation of the muscles associated with the small intestine 38's target portion may be help move the contents of the small intestine 38 in a proximal to caudad direction, such as by causing all, or part, of the muscles associated with the small intestine 38's target portion to contract simultaneously, or by causing all, or part, of them to sequentially contract in a proximal to caudad direction.

The anticonstipation apparatus of the present invention may also be used to treat constipation of the stomach 40. Thus, the target portion of the stomach 40 may comprise all, or part, of the stomach 40. Electrically stimulating the muscles associated with the stomach 40's target portion may be done in a manner which may be the same as, or similar to, that described above regarding electrically stimulating the muscles associated with the descending colon's target portion 17. Thus, such stimulation may be provided by stomach electrodes 41, 41a, 41b that may be the same as, or similar to, the electrodes 14, 14a, 14b, respectively. The electrodes 41, 41a, 41b may be connected to the stimulus generator 10 through a lead 12f that may be the same as, or similar to the leads 12, 12a and 12b. If the lead 12f has an electrode portion 11f and a connecting portion 15f, they may be the same as, or similar to, the electrode portion 11 and the connecting portion 15, respectively, of the lead 12. The electrode portion 11f may include constipation sensing means 21f, 28f, that may be the same as, or similar to, the constipation sensing means 21, 28 of the lead 12. The electrode portion 11f may be located on the greater curvature of the stomach 40. The electrical leads for the constipation sensing means 21f, 28f may be the same as, or similar to, the electrical leads for the sensing means 21, 28, respectively.

A goal of such stimulation of the muscles associated with the stomach 40's target portion may be to help move the contents of the stomach 40 in a proximal to caudad direction, such as by causing all, or part, of the stimulated muscles to contract simultaneously, or by causing all, or part, of the stimulated muscles to sequentially contract in a proximal to caudad direction.

The anticonstipation apparatus of the present invention may also be used to treat "constipation" of the esophagus 42. Thus, the target portion of the esophagus 42 may comprise all, or part, of the esophagus 42. Electrically stimulating the muscles associated with the esophagus 42's target portion may be done in a manner which may be the same as, or similar to, that described above regarding stimulating the muscles associated with the descending colon's target portion 17. Thus, such stimulation may be provided by esophagus electrodes 43, 43a, 43b that may be the same as, or similar to, the electrodes 14, 14a, 14b, respectively. The electrodes 43, 43a, 43b may be connected to the stimulus generator 10 through a lead 12g that may be the same as, or similar to the leads 12, 12a and 12b. If the lead 12g has an electrode portion 11g and a connecting portion 15g, they may be the same as, or similar to, the electrode portion 11 and the connecting portion 15, respectively, of the lead 12. The electrode portion 11g may include constipation sensing means 21g, 28g, that may be the same as, or similar to, the constipation sensing means 21, 28 of the lead 12. The electrical leads for the constipation sensing means 21g, 28g may be the same as, or similar to, the electrical leads for the sensing means 21, 28, respectively.

A goal of such stimulation of the muscles of the esophagus 42's target portion may be to help move the contents of the esophagus 42 in a proximal to caudad direction, such as by causing all, or part, of the stimulated muscles to contract simultaneously, or by causing all, or part, of the stimulated muscles to sequentially contract in a proximal to caudad direction.

It is understood that the foregoing forms of the invention were described and/or illustrated strictly by way of non-limiting example.

In view of all of the disclosures herein, these and further modifications, adaptations and variations of the present invention will now be apparent to those skilled in the art to which it pertains, within the scope of the following claims.

What is claimed is:

1. An anticonstipation apparatus for treating constipation in a human patient, comprising:

electrode means for delivering sequential electrical stimulation to muscles that are associated with a target portion of the gut of said patient;

stimulus generator means for generating said sequential electrical stimulation; and electrical lead means adapted to convey said sequential electrical stimulation from said stimulus generator means to said electrode means;

wherein said muscles are located sequentially with respect to each other in a proximal to caudad direction and the electrode means are adapted to stimulate same;

wherein said sequential electrical stimulation is selected to urge said muscles to sequentially contract, in said proximal to caudad direction, to urge at least a portion of the contents of said target portion to move in said proximal to caudad direction, and wherein said electrical lead means comprises an electrical lead, said electrical lead comprising an electrode portion having a flexible, flat, ribbon-like configuration, at least a portion of said electrode means being located on a first face of said electrode portion wherein said electrode means further comprises from two to 100 pairs of electrodes.

2. The anticonstipation apparatus according to claim 1, wherein at least some of said muscles are located in a wall of said target portion; and wherein at least portions of said electrode means are configured and adapted to deliver said sequential electrical stimulation directly to said muscles located in said wall.

3. The anticonstipation apparatus according to claim 1, wherein at least portions of said electrode means are configured and adapted to deliver said electrical stimulation to at least one portion of the autonomic nervous system associated with at least some of said muscles.

4. The anticonstipation apparatus according to claim 1:
wherein said apparatus further comprises constipation sensing means for sensing when at least a portion of said target portion is constipated, and for generating a constipated signal when at least a portion of said target portion is constipated;
wherein at least portions of said electrical lead means are configured and adapted to deliver said constipated signal from said constipation sensing means to said stimulus generator means; and
wherein said stimulus generator means is configured to commence said delivery of said sequential electrical stimulation, after receiving said constipated signal from said constipation sensing means.

5. The anticonstipation apparatus according to claim 4, wherein said constipation sensing means further comprises a motion sensor means for sensing any peristaltic waves generated by said target portion.

6. The anticonstipation apparatus according to claim 4, wherein said constipation sensing means further comprises a pressure sensor means for sensing the pressure within said target portion.

7. The anticonstipation apparatus according to claim 4, wherein said constipation sensing means further comprises a strain gauge means for sensing the tension in a wall of said target portion.

8. The anticonstipation apparatus according to claim 4, wherein said constipation sensing means further comprises impedance sensing means for sensing the impedance of at least a portion of a wall of said target portion.

9. The anticonstipation apparatus according to claim 4, wherein said constipation sensing means further comprises a saddle means for sensing the shape of a wall of said target portion.

10. The anticonstipation apparatus according to claim 1, wherein said electrodes in at least one of said pairs of electrodes are generally rectangular, have a width in the range of from about 1 mm to about 10 mm, and a length in the range of from about 2 mm to about 20 mm.

11. The anticonstipation apparatus according to claim 1, wherein said electrodes in at least one of said pairs of electrodes have a separation from each other in the range of from about 1 mm to about 100 mm.

12. The anticonstipation apparatus according to claim 1, wherein at least two pairs of said electrodes have a separation from each other in the range of from about 1 cm to about 10 cm.

13. The anticonstipation apparatus according to claim 1, wherein said sequential electrical stimulation is delivered sequentially to at least two pairs of said electrodes in said proximal to caudad direction.

14. The anticonstipation apparatus according to claim 1, wherein said target portion further comprises at least a portion of the colon of said patient.

15. The anticonstipation apparatus according to claim 1, wherein said target portion further comprises a first target portion comprising at least a portion of the descending colon of said patient.

16. The anticonstipation apparatus according to claim 15, wherein said target portion further comprises a second target portion comprising at least a portion of the rectum of said patient.

17. The anticonstipation apparatus according to claim 16, wherein said sequential electrical stimulation is delivered to said muscles associated with said first target portion, before said sequential electrical stimulation is delivered to said muscles associated with said second target portion, to urge at least a portion of the contents of said first and second target portions to move sequentially from said first target portion to said second target portion, in said proximal to caudad direction.

18. The anticonstipation apparatus according to claim 1, wherein said target portion further comprises at least a portion of the small intestine of said patient.

19. The anticonstipation apparatus according to claim 1, wherein said target portion further comprises at least a portion of the stomach of said patient.

20. The anticonstipation apparatus according to claim 1, wherein said target portion further comprises at least a portion of the esophagus of said patient.

21. The anticonstipation apparatus according to claim 1, wherein said sequential electrical stimulation further comprises at least two sequential electrical stimuli; and wherein at least one of said stimuli has a voltage in the range of from about 20 microvolts to about 50 volts.

22. The anticonstipation apparatus according to claim 1, wherein said sequential electrical stimulation further comprises at least two sequential electrical stimuli; and wherein at least one of said stimuli has a duration in the range of from about 20 microseconds to about 20 milliseconds.

23. The anticonstipation apparatus according to claim 1, wherein said sequential electrical stimulation further comprises at least two sequential electrical stimuli; and wherein at least one of said stimuli comprises at least one uniphasic electrical stimulus.

24. The anticonstipation apparatus according to claim 1, wherein said sequential electrical stimulation further comprises at least two sequential electrical stimuli; and wherein at least one of said stimuli comprises at least one biphasic electrical stimulus.

25. The anticonstipation apparatus according to claim 1, wherein said sequential electrical stimulation further comprises at least two sequential electrical stimuli; and wherein at least one of said stimuli comprises at least one multiphasic electrical stimulus.

26. The anticonstipation apparatus according to claim 1, wherein said sequential electrical stimulation further comprises from one to ten sets of sequential electrical stimuli.

27. The anticonstipation apparatus according to claim 26:
wherein each said set of sequential electrical stimuli further comprises from two to one hundred sequential included electrical stimuli; and
wherein said sequential included electrical stimuli further are delivered sequentially to respective pairs of said electrodes.

28. The anticonstipation apparatus according to claim 27, wherein at least one of said sequential included electrical stimuli further comprises from one to about 100 electrical pulses.

29. The anticonstipation apparatus according to claim 1:
wherein said sequential electrical stimulation further comprises at least two sets of sequential electrical stimuli; and
wherein said at least two sets of sequential electrical stimuli further have a separation from each other in the range of from about 20 microseconds to about 60 seconds.

30. An anticonstipation method for treating constipation in a human patient, wherein an implantable electrical lead means comprising electrode means is employed in said method, said electrical lead comprising an electrode portion having a flexible, flat, ribbon-like configuration, at least a portion of said electrode means being located on a first face of said electrode portion, said method comprising the steps of:

selecting muscles that are associated with a target portion of the gut of said patient, wherein said muscles are located sequentially with respect to each other in said proximal to caudad direction;

implanting in said patient said electrode means for delivering sequential electrical stimulation to said muscles;

selecting said sequential electrical stimulation to urge said muscles to sequentially contract, in said proximal to caudad direction, to urge at least a portion of the contents of said target portion to move in said proximal to caudad direction; and delivering said sequential electrical stimulation to said muscles by using said electrode means.

31. A method according to claim 30:

wherein said selecting muscles step further comprises the step of selecting at least some of said muscles to be located in the wall of said target portion; and wherein said implanting step further comprises implanting said electrode means in a location selected to enable said electrode means to deliver said electrical stimulation directly to said muscles that are located in a wall.

32. A method according to claim 30, wherein said implanting step further comprises the step of implanting said electrode means in a location selected to enable said electrode means to deliver said electrical stimulation to at least one portion of the autonomic nervous system associated with at least some of said muscles.

33. A method according to claim 30, further comprising the steps of:

implanting in said patient constipation sensing means for sensing when at least a portion of said target portion is constipated, and for generating a constipated signal when at least a portion of said target portion is constipated; and commencing said delivering step after said constipation sensing means has generated said constipated signal.

34. A method according to claim 30, wherein said selecting muscles step further comprises the step of selecting said target portion to comprise a first target portion comprising at least a portion of the descending colon of said patient.

35. A method according to claim 34, wherein said selecting muscles step further comprises the step of selecting said target portion to comprise a second target portion comprising at least a portion of the rectum of said patient.

36. A method according to claim 35, wherein said delivering step further comprises the steps of first delivering said sequential electrical stimulation to said muscles associated with said first target portion, and then delivering said sequential electrical stimulation to said muscles associated with said second target portion, to urge at least a portion of the contents of said first and second target portions to move from said first target portion to said second target portion, in said proximal to caudad direction.

37. An anticonstipation apparatus for treating constipation in a human patient, wherein said apparatus comprises:

electrode means for delivering electrical stimulation to muscles that are associated with a target portion of the gut of said patient;

stimulus generator means for generating said electrical stimulation; and electrical lead means for conveying said electrical stimulation from said stimulus generator means to said electrode means;

wherein said electrical stimulation is selected to urge said muscles to contract, to urge at least a portion of the contents of said target portion to move in a proximal to caudad direction, and said electrical lead means comprises an electrical lead, said electrical lead comprising an electrode portion having a flexible, flat, ribbon-like configuration, at least a portion of said electrode means being located on a first face of said electrode portion wherein said electrode means further comprises from two to 100 pairs of electrodes.

38. The anticonstipation apparatus according to claim 37, wherein at least some of said muscles are located in the wall of said target portion, and said electrode means is for delivering said electrical stimulation directly to said muscles that are located in a wall.

39. The anticonstipation apparatus according to claim 37, wherein said electrode means is for delivering said electrical stimulation to at least one portion of the autonomic nervous system that is associated with at least some of said muscles.

40. The anticonstipation apparatus according to claim 37:

wherein said apparatus further comprises constipation sensing means for sensing when at least a portion of said target portion is constipated, and for generating a constipated signal when at least a portion of said target portion is constipated;

wherein said electrical lead means is also for delivering said "constipated" signal from said constipation sensing means to said stimulus generator means; and wherein said stimulus generator means is also for commencing said delivering of said electrical stimulation, after receiving said constipated signal from said constipation sensing means.

41. The anticonstipation apparatus according to claim 40, wherein said constipation sensing means comprises a motion sensor means for sensing any peristaltic waves generated by said target portion.

42. The anticonstipation apparatus according to claim 40, wherein said constipation sensing means comprises a pressure sensor means for sensing the pressure within said target portion.

43. The anticonstipation apparatus according to claim 40, wherein said constipation sensing means comprises a strain gauge means for sensing the tension in a wall of said target portion.

44. The anticonstipation apparatus according to claim 40, wherein said constipation sensing means comprises impedance sensing means for sensing the impedance of at least a portion of a wall of said target portion.

45. The anticonstipation apparatus according to claim 40, wherein said constipation sensing means comprises a saddle means for sensing the shape of a wall of said target portion.

46. The anticonstipation apparatus according to claim 37, wherein at least one of said electrodes is generally rectangular, having a width in the range of from about 1 mm to about 10 mm, and having a length in the range of from about 2 mm to about 20 mm.

47. The anticonstipation apparatus according to claim 46, wherein said electrodes in a pair of electrodes have a separation from each other in the range of from about 1 mm to about 100 mm.

48. The anticonstipation apparatus according to claim 37, wherein said target portion comprises at least a portion of the colon of said patient.

49. The anticonstipation apparatus according to claim 37, wherein said target portion comprises a first target portion comprising at least a portion of the descending colon of said patient.

50. The anticonstipation apparatus according to claim 49, wherein said target portion further comprises a second target portion comprising at least a portion of the rectum of said patient.

51. The anticonstipation apparatus according to claim 50, wherein said electrical stimulation is delivered to said muscles that are associated with said first target portion, before said electrical stimulation is delivered to said muscles that are associated with said second target portion, to urge at least a portion of the contents of said first and second target portions to move sequentially from said first target portion to said second target portion, in said proximal to caudad direction.

52. The anticonstipation apparatus according to claim 37, wherein said target portion comprises at least a portion of the small intestine of said patient.

53. The anticonstipation apparatus according to claim 37, wherein said target portion comprises at least a portion of the stomach of said patient.

54. The anticonstipation apparatus according to claim 37, wherein said target portion comprises at least a portion of the esophagus of said patient.

55. The anticonstipation apparatus according to claim 37, wherein said electrical stimulation comprises at least one electrical stimulus having a voltage in the range of from about 20 microvolts to about 50 volts.

56. The anticonstipation apparatus according to claim 37, wherein said electrical stimulation comprises at least one electrical stimulus having a duration in the range of from about 20 microseconds to about 20 milliseconds.

57. The anticonstipation apparatus according to claim 37, wherein said electrical stimulation comprises at least one electrical stimulus comprising at least one uniphasic electrical stimulus.

58. The anticonstipation apparatus according to claim 37, wherein said electrical stimulation comprises at least one electrical stimulus comprising at least one biphasic electrical stimulus.

59. The anticonstipation apparatus according to claim 37, wherein said electrical stimulation comprises at least one electrical stimulus comprising at least one multiphasic electrical stimulus.

60. The anticonstipation apparatus according to claim 37, wherein said electrical stimulation comprises from one to about ten sets of electrical stimuli.

61. The anticonstipation apparatus according to claim 60, wherein each said set of electrical stimuli comprises from one to about one hundred included electrical stimuli.

62. The anticonstipation apparatus according to claim 61, wherein at least one of said included electrical stimuli comprises from one to about 100 electrical pulses.

63. The anticonstipation apparatus according to claim 37:
wherein said electrical stimulation comprises at least two sets of electrical stimuli; and
wherein said at least two sets of electrical stimuli have a separation from each other in the range of from about 20 microseconds to about 60 seconds.

64. An anticonstipation method for treating constipation in a human patient, wherein an implantable electrical lead means comprising electrode means is employed in said method, said electrical lead comprising an electrode portion having a flexible, flat, ribbon-like configuration, at least a portion of said electrode means being located on a first face of said electrode portion, said method comprising the steps of:
selecting muscles that are associated with a target portion of the gut of said patient;
implanting in said patient electrode means for delivering electrical stimulation to said muscles;
selecting said electrical stimulation to urge said muscles to contract, to urge at least a portion of the contents of said target portion to move in a proximal to caudad direction; and
delivering said electrical stimulation to said muscles by using said electrode means.

65. A method according to claim 64:
wherein said selecting muscles step further comprises the step of selecting at least some of said muscles to be located in a wall of said target portion, and
wherein said implanting step further comprises implanting said electrode means in a location selected to enable said electrode means to deliver said electrical stimulation directly to said muscles that are located in said wall.

66. A method according to claim 64, wherein said implanting step further comprises the step of implanting said electrode means in a location selected to enable said electrode means to deliver said electrical stimulation to at least one portion of the autonomic nervous system that is associated with at least some of said muscles.

67. A method according to claim 64, further comprising the steps of:
implanting in said patient constipation sensing means for sensing when at least a portion of said target portion is constipated, and for generating a constipated signal when at least a portion of said target portion is constipated; and
commencing said delivering step after said constipation sensing means has generated said constipated signal.

68. A method according to claim 64, wherein said selecting muscles step further comprises the step of selecting said target portion to comprise a first target portion comprising at least a portion of the descending colon of said patient.

69. A method according to claim 68, wherein said selecting muscles step further comprises the step of selecting said target portion to comprise a second target portion comprising at least a portion of the rectum of said patient.

70. A method according to claim 69, wherein said delivering step further comprises the steps of first delivering said electrical stimulation to said muscles that are associated with said first target portion, and then delivering said electrical stimulation to said muscles that are associated with said second target portion, to urge at least a portion of the contents of said first and second target portions to move from said first target portion to said second target portion, in said proximal to caudad direction.

* * * * *